(12) United States Patent
Williams

(10) Patent No.: US 9,874,528 B2
(45) Date of Patent: Jan. 23, 2018

(54) PORTABLE CONTACT ANGLE MEASURING KIT

(71) Applicant: Sam Houston State University, Huntsville, TX (US)

(72) Inventor: Darren L. Williams, Huntsville, TX (US)

(73) Assignee: Sam Houston State University, Huntsville, TX (US)

( * ) Notice: Subject to any disclaimer, the term of this patent is extended or adjusted under 35 U.S.C. 154(b) by 0 days.

(21) Appl. No.: 14/933,386

(22) Filed: Nov. 5, 2015

(65) Prior Publication Data

US 2016/0140735 A1    May 19, 2016

Related U.S. Application Data

(60) Provisional application No. 62/079,053, filed on Nov. 13, 2014.

(51) Int. Cl.
*G01B 11/22* (2006.01)
*H04N 7/18* (2006.01)
*H04N 5/232* (2006.01)
*G01N 21/94* (2006.01)

(52) U.S. Cl.
CPC ..... *G01N 21/94* (2013.01); *G01N 2201/0221* (2013.01)

(58) Field of Classification Search
CPC .......... G01B 11/26; G01N 13/02; G01N 2013/0208; G01N 21/8851; G01N 21/94; G01N 13/00
USPC ............................... 356/627; 348/135, 349
See application file for complete search history.

(56) References Cited

U.S. PATENT DOCUMENTS

| 3,972,132 A | 8/1976 | Slomski |
| 4,050,822 A * | 9/1977 | Grat ................. G01N 13/02 356/397 |
| 4,977,853 A | 12/1990 | Falcoff et al. |
| 6,088,116 A | 7/2000 | Pfanstiehl |
| 7,639,862 B2 | 12/2009 | Canning, Jr. et al. |
| 2002/0115224 A1 * | 8/2002 | Rudel ................. B01J 19/0046 436/164 |

(Continued)

OTHER PUBLICATIONS

Williams, D. et al. "Contact Angle Measurements Using Cellphone Cameras to Implement the Bikerman Method" Galvanotechnik Aug. 2011, pp. 1718-1725.

*Primary Examiner* — Sunghee Y Gray
(74) *Attorney, Agent, or Firm* — Meyertons, Hood, Kivlin Kowert & Goetzel, P.C.; Mark R. DeLuca

(57) ABSTRACT

In some embodiments, a system and/or method may include assessing surface cleanliness. In some embodiments, the system may include a dispensing device. The dispensing device may dispense, during use, a measured amount of liquid on a surface forming a drop. In some embodiments, the system may include a stage. The stage may support, during use, a digital imaging device. In some embodiments, the system may include a calibration feature. The calibration feature may be of known dimension. The calibration feature may be coupled to the stage. The calibration feature may facilitate assessment, during use, of a dimension of the drop. The dimension may include a diameter of the drop. In some embodiments, the system is configured to assess a contact angle of the drop with the surface.

16 Claims, 3 Drawing Sheets

(56) References Cited

U.S. PATENT DOCUMENTS

| | | | |
|---|---|---|---|
| 2004/0012676 A1* | 1/2004 | Weiner | G01N 21/253 348/207.1 |
| 2007/0146702 A1 | 6/2007 | Canning, Jr. et al. | |
| 2008/0018909 A1* | 1/2008 | Osaka | G01B 11/08 356/521 |
| 2010/0024529 A1* | 2/2010 | Dillingham | G01N 13/02 73/64.52 |

* cited by examiner

PORTABLE CONTACT ANGLE MEASURING KIT

PRIORITY CLAIM

This application claims priority to U.S. Provisional Patent Application No. 62/079,053 entitled "PORTABLE CONTACT ANGLE MEASURING KIT" filed on Nov. 13, 2014, which is incorporated by reference herein.

BACKGROUND OF THE INVENTION

1. Field of the Invention

The present disclosure generally relates to assessing surface cleanliness. More particularly, the disclosure generally relates to a portable system and method for measuring a contact angle between a droplet of liquid and a surface.

2. Description of the Relevant Art

There are many instances where a surface must be cleaned sufficiently to permit a following operation to be conducted. For example, a surface that is to be coated (e.g., paint) must first have contaminants (e.g., oil, particulate matter, etc.) removed from the surface so that the coating to be applied will adhere properly to the surface. Proper surface cleanliness is especially important for a smooth metallic surface (e.g., planes, cars, trucks, etc.). Surface irregularities resulting from contamination minimizes coating adhesion through the keying action between the coating film and surface irregularities. Coating adhesion in such cases depends substantially on other adherent mechanisms such as molecular attraction between the metallic surface and the applied coating, and good molecular bonding is achieved only when the surface is properly free of contamination.

The cost of cleaning a surface to be painted increases when the surface being cleaned is part of a large assembled structure. While a surface can be deliberately cleaned beyond the minimum extent necessary for the desired coating adhesion, the expense of such excessive cleaning of the surface is counterproductive.

The measurement of contact angle began in 1805 with the work of Thomas Young. Since then there have been many papers published using contact angle or suggesting new ways to measure contact angle. Almost all of these methods are focused on small samples that may be brought to the lab for analysis in a contact angle measuring device. The field appropriate analyses are mainly the Bikerman method of viewing a drop from above, the Langmuir method of viewing the angle of reflected light from the drop surface, and the drop-shape analysis methods that view the drop from the side. All of these methods have been successfully used in the laboratory. The utility of this method has been revisited recently to show its compatibility and improvement with modern cell phone cameras, macro lenses, and computer spreadsheet programs. But to date, no known source exists that provides the various parts in a self-calibrating contact angle measurement kit that would enable the user to utilize these field-appropriate methods.

SUMMARY

In some embodiments, a system and/or method may include assessing surface cleanliness. In some embodiments, the system may include a dispensing device. The dispensing device may dispense, during use, a measured amount of liquid on a surface forming a drop. In some embodiments, the system may include a stage. The stage may support, during use, a digital imaging device. In some embodiments, the system may include a calibration feature. The calibration feature may be of known dimension. The calibration feature may be coupled to the stage. The calibration feature may facilitate assessment, during use, of a dimension of the drop. The dimension may include a diameter of the drop. In some embodiments, the system is configured to assess a contact angle of the drop with the surface.

In some embodiments, a distance between the stage and the calibration feature may be determined by a focal length of the digital imaging device. The stage may include a macro lens. A distance between the stage and the calibration feature may be determined by a focal length of the macro lens. The stage may include the digital imaging device (e.g., be formed as part of the stage). In some embodiments, a distance between the stage and the calibration feature is adjustable and determined by a focal length of the digital imaging device.

In some embodiments, the digital imaging device comprises a multi-function device (e.g. cellular phone, mini-computer, tablet).

In some embodiments, the system may be configured to assess cleanliness or surface energy of the surface. In some embodiments, the system may be configured to assess a contact angle of the drop with the surface. In some embodiments, the calibration feature may include a tapered edge.

In some embodiments, a method may include assessing surface cleanliness. The method may include dispensing a measured amount of liquid on a surface forming a drop using a dispensing device. The method may include supporting a digital imaging device using a stage. The method may include assessing a dimension of the drop using a calibration feature of known dimension coupled to the stage. The method may include determining a distance between the stage and the calibration feature using a focal length of the digital imaging device. The method may include adjusting a distance between the stage and the calibration feature using a focal length of the digital imaging device. The method may include assessing a contact angle of the drop with the surface. The method may include assessing a cleanliness of the surface.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
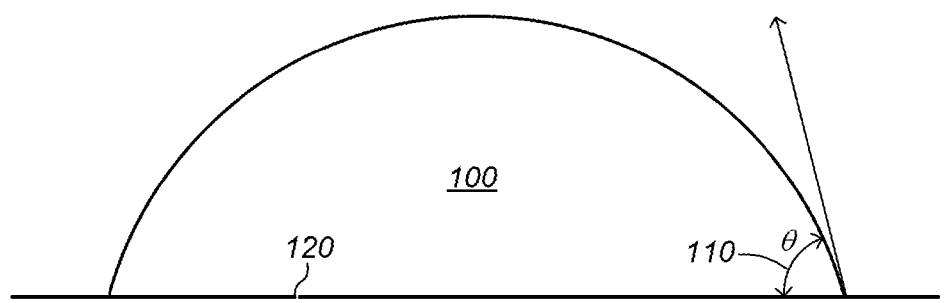
FIG. 1 depicts a perspective view of a representation of an embodiment of a sessile drop showing the definition of contact angle θ.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicate open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. §112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

In some embodiments, a system and/or method may include assessing surface cleanliness. In some embodiments, a system may measure a contact angle of a sessile drop. The sessile drop technique is a method used for the characterization of solid surface energies and aspects of liquid surface energies. The main premise of the method is that by placing a droplet of liquid with a known surface energy, the shape of the drop, specifically the contact angle, and the known surface energy of the liquid are the parameters which can be used to calculate the surface energy of the solid sample.

In 1941, Bikerman proposed a novel method of measuring the contact angle of a sessile drop. This was based on viewing the droplet from above and measuring the diameter of the droplet, on known volume. For small volume spherical drops, he derived the equation [1]:

$$d^3/v = (24 \sin^3\theta)/(\pi(2 - 3\cos\theta + \cos^3\theta)) \quad [1]$$

Where d is the diameter of the base of the drop, sometimes referred to as the contact diameter, v is the volume of the drop, and θ is the contact angle. FIG. 1 depicts a perspective view of a representation of an embodiment of a sessile drop 100 showing the definition of contact angle θ 110 with a surface 120.

In the Bikerman equation, the term d is the diameter of the droplet base—the circular contact area made by the drop on the surface on which it rests. For contact angles that are less than 90°, where the drop is a hemisphere or less, d is readily measured by viewing the drop from above. However for contact angles greater than 90°, where the drop is greater than hemi-spherical, the maximum girth of the drop will be greater than its contact diameter, such that it will overhang the contact area and obscure it from view. Thus, the Bikerman equation must be modified slightly for use with contact angles>90° such that the waist diameter (w in equation [2]) of the drop is used instead of the base diameter d.

$$w^3/v = 24/(\pi(2 - 3\cos\theta + \cos^3\theta)) \quad [2]$$

A simple mathematical test identifies situations where the contact angle is less than 90° and where, in consequence the original Bikerman equation [1] or the modified equation [2] can be used with direct overhead viewing. If the measured diameter is greater than the 90°-diameter (d90) (Eq. [3]), then it is valid to use equation [1] otherwise equation [2] should be used.

$$d90 = (12v/\pi)^{1/3} \quad [3]$$

where d90 is the diameter of a hemisphere of volume v. Incorporating this validity test (Eq. [3]), the authors have used computer spreadsheets and cell phone cameras to implement the Bikerman method with minimal cost and analysis time. The availability of computer spreadsheets is perhaps the most important factor in making the Bikerman method more user-friendly. The authors offer a spreadsheet (Tab. 1) that accepts user input of individual volume and diameter values, calculating the contact angle using a lookup-table of the Bikerman equation with 0.10° increments over the range of θ of 0.10° to 179.90°. The spreadsheet applies the test noted above (Eq. [3]), and uses the appropriate version of the Bikerman equation.

The spreadsheet can also be used to generate nomogram sheets (hard copy printouts of the Bikerman equations) for the graphical determination of contact angle. The validity test of equation [3] may be used on this worksheet. Lastly, if the user provides uncertainty values, the spreadsheet will compute the uncertainty in contact angle using equation [4], which was derived using standard propagation of uncertainty techniques.

$$s_{d^3/v} = \frac{d^3}{v}\left(3\left(\frac{s_{C_{px}}}{C_{px}}\right)^2 + 3\left(\frac{s_{C_{cm}}}{C_{cm}}\right)^2 + 3\left(\frac{s_{d_{px}}}{d_{px}}\right)^2 + \left(\frac{s_v}{v}\right)^2\right)^{\frac{1}{2}} \quad [4]$$

Where $s_{d^3/v}$ is the uncertainty in the d3/v term, sd is the uncertainty in the diameter measurement (d), and sv is the uncertainty in the drop volume (v). The calibration object (C) is measured in pixels and in cm. The px subscripts in equation [4] indicate an image analysis measurement in pixels. Equation [4] also applies to the modified Bikerman equation [2] if all base diameter d values in equation [4] are substituted with waist diameter w values. The image analysis will be further explained by a description of the various measurement methods.

There are slight differences in the positive and negative uncertainties of contact angle because of the non non-linear nature of the Bikerman equation. To account for this, the uncertainty in contact angle is calculated by looking up the positive and negative deviations separately using the Bikerman lookup-table (Tab. 1).

TABLE 1

| w3/v (unitless) | Θ Lookup (deg) | d3/v (unitless) | Θ Lookup (deg) |
|---|---|---|---|
| 1.9098593171 | 179.90 | 3.8197 | 90.00 |
| 1.9098593172 | 179.80 | 3.8297 | 89.90 |
| 1.9098593174 | 179.70 | 3.8398 | 89.80 |
| 1.909859318 | 179.60 | 3.8498 | 89.70 |
| 1.909859319 | 179.50 | 3.8599 | 89.60 |
| 1.909859321 | 179.40 | 3.8699 | 89.50 |
| 1.909859325 | 179.30 | 3.8800 | 89.40 |
| 1.909859331 | 179.20 | 3.8901 | 89.30 |
| 1.90985934 | 179.10 | 3.9003 | 89.20 |
| 1.90985935 | 179.00 | 3.9104 | 89.10 |
| 1.90985937 | 178.90 | 3.9206 | 89.00 |
| 1.90985939 | 178.80 | 3.9308 | 88.90 |
| 1.90985941 | 178.70 | 3.9410 | 88.80 |
| 1.90985944 | 178.60 | 3.9512 | 88.70 |
| 1.90985949 | 178.50 | 3.9615 | 88.60 |
| 1.90985953 | 178.40 | 3.9717 | 88.50 |
| 1.90985959 | 178.30 | 3.9820 | 88.40 |
| 1.90985967 | 178.20 | 3.9923 | 88.30 |
| 1.9098597 | 178.10 | 4.0026 | 88.20 |
| 1.9098598 | 178.00 | 4.0129 | 88.10 |
| 1.9098600 | 177.90 | 4.0233 | 88.00 |
| 1.9098601 | 177.80 | 4.0336 | 87.90 |
| 1.9098602 | 177.70 | 4.0440 | 87.80 |

TABLE 1-continued

| w3/v (unitless) | Θ Lookup (deg) | d3/v (unitless) | Θ Lookup (deg) |
|---|---|---|---|
| 1.9098604 | 177.60 | 4.0544 | 87.70 |
| 1.9098606 | 177.50 | 4.0649 | 87.60 |
| 1.9098608 | 177.40 | 4.0753 | 87.50 |
| 1.9098611 | 177.30 | 4.0858 | 87.40 |
| 1.9098614 | 177.20 | 4.0962 | 87.30 |
| 1.9098617 | 177.10 | 4.1067 | 87.20 |
| 1.9098620 | 177.00 | 4.1173 | 87.10 |
| 1.9098624 | 176.90 | 4.1278 | 87.00 |
| 1.9098628 | 176.80 | 4.1383 | 86.90 |
| 1.9098633 | 176.70 | 4.1489 | 86.80 |
| 1.9098638 | 176.60 | 4.1595 | 86.70 |
| 1.9098643 | 176.50 | 4.1701 | 86.60 |
| 1.9098649 | 176.40 | 4.1808 | 86.50 |
| 1.9098655 | 176.30 | 4.1914 | 86.40 |
| 1.909866 | 176.20 | 4.2021 | 86.30 |
| 1.909867 | 176.10 | 4.2128 | 86.20 |
| 1.909868 | 176.00 | 4.2235 | 86.10 |
| 1.909869 | 175.90 | 4.2342 | 86.00 |
| 1.909870 | 175.80 | 4.2449 | 85.90 |
| 1.909871 | 175.70 | 4.2557 | 85.80 |
| 1.909872 | 175.60 | 4.2665 | 85.70 |
| 1.909873 | 175.50 | 4.2773 | 85.60 |
| 1.909874 | 175.40 | 4.2881 | 85.50 |
| 1.909875 | 175.30 | 4.2990 | 85.40 |
| 1.909877 | 175.20 | 4.3098 | 85.30 |
| 1.909878 | 175.10 | 4.3207 | 85.20 |
| 1.909880 | 175.00 | 4.3316 | 85.10 |
| 1.909882 | 174.90 | 4.3426 | 85.00 |
| 1.909884 | 174.80 | 4.3535 | 84.90 |
| 1.909885 | 174.70 | 4.3645 | 84.80 |
| 1.909887 | 174.60 | 4.3755 | 84.70 |
| 1.909890 | 174.50 | 4.3865 | 84.60 |
| 1.909892 | 174.40 | 4.3975 | 84.50 |
| 1.909894 | 174.30 | 4.4085 | 84.40 |
| 1.909897 | 174.20 | 4.4196 | 84.30 |
| 1.909899 | 174.10 | 4.4307 | 84.20 |
| 1.909902 | 174.00 | 4.4418 | 84.10 |
| 1.909905 | 173.90 | 4.4529 | 84.00 |
| 1.909908 | 173.80 | 4.4641 | 83.90 |
| 1.909911 | 173.70 | 4.4753 | 83.80 |
| 1.909915 | 173.60 | 4.4864 | 83.70 |
| 1.909918 | 173.50 | 4.4977 | 83.60 |
| 1.909922 | 173.40 | 4.5089 | 83.50 |
| 1.909926 | 173.30 | 4.5201 | 83.40 |
| 1.909930 | 173.20 | 4.5314 | 83.30 |
| 1.909934 | 173.10 | 4.5427 | 83.20 |
| 1.909939 | 173.00 | 4.5540 | 83.10 |
| 1.909943 | 172.90 | 4.5654 | 83.00 |
| 1.909948 | 172.80 | 4.5767 | 82.90 |
| 1.909953 | 172.70 | 4.5881 | 82.80 |
| 1.909958 | 172.60 | 4.5995 | 82.70 |
| 1.909964 | 172.50 | 4.6109 | 82.60 |
| 1.909970 | 172.40 | 4.6224 | 82.50 |
| 1.909975 | 172.30 | 4.6339 | 82.40 |
| 1.909982 | 172.20 | 4.6454 | 82.30 |
| 1.909988 | 172.10 | 4.6569 | 82.20 |
| 1.909995 | 172.00 | 4.6684 | 82.10 |
| 1.910001 | 171.90 | 4.6800 | 82.00 |
| 1.910009 | 171.80 | 4.6915 | 81.90 |
| 1.910016 | 171.70 | 4.7031 | 81.80 |
| 1.910024 | 171.60 | 4.7148 | 81.70 |
| 1.910032 | 171.50 | 4.7264 | 81.60 |
| 1.910040 | 171.40 | 4.7381 | 81.50 |
| 1.910048 | 171.30 | 4.7498 | 81.40 |
| 1.91006 | 171.20 | 4.7615 | 81.30 |
| 1.91007 | 171.10 | 4.7732 | 81.20 |
| 1.91008 | 171.00 | 4.7850 | 81.10 |
| 1.91009 | 170.90 | 4.7968 | 81.00 |
| 1.91010 | 170.80 | 4.8086 | 80.90 |
| 1.91011 | 170.70 | 4.8204 | 80.80 |
| 1.91012 | 170.60 | 4.8322 | 80.70 |
| 1.91013 | 170.50 | 4.8441 | 80.60 |
| 1.91014 | 170.40 | 4.8560 | 80.50 |
| 1.91015 | 170.30 | 4.8679 | 80.40 |
| 1.91016 | 170.20 | 4.8799 | 80.30 |
| 1.91018 | 170.10 | 4.8918 | 80.20 |
| 1.91019 | 170.00 | 4.9038 | 80.10 |
| 1.91020 | 169.90 | 4.9158 | 80.00 |

TABLE 1-continued

| w3/v (unitless) | Θ Lookup (deg) | d3/v (unitless) | Θ Lookup (deg) |
|---|---|---|---|
| 1.91022 | 169.80 | 4.9279 | 79.90 |
| 1.91023 | 169.70 | 4.9399 | 79.80 |
| 1.91024 | 169.60 | 4.9520 | 79.70 |
| 1.91026 | 169.50 | 4.9641 | 79.60 |
| 1.91027 | 169.40 | 4.9762 | 79.50 |
| 1.91029 | 169.30 | 4.9884 | 79.40 |
| 1.91031 | 169.20 | 5.0006 | 79.30 |
| 1.91032 | 169.10 | 5.0128 | 79.20 |
| 1.91034 | 169.00 | 5.0250 | 79.10 |
| 1.91036 | 168.90 | 5.0373 | 79.00 |
| 1.91038 | 168.80 | 5.0495 | 78.90 |
| 1.91039 | 168.70 | 5.0618 | 78.80 |
| 1.91041 | 168.60 | 5.0742 | 78.70 |
| 1.91043 | 168.50 | 5.0865 | 78.60 |
| 1.91045 | 168.40 | 5.0989 | 78.50 |
| 1.91047 | 168.30 | 5.1113 | 78.40 |
| 1.91049 | 168.20 | 5.1237 | 78.30 |
| 1.91052 | 168.10 | 5.1362 | 78.20 |
| 1.91054 | 168.00 | 5.1486 | 78.10 |
| 1.91056 | 167.90 | 5.1611 | 78.00 |
| 1.91058 | 167.80 | 5.1737 | 77.90 |
| 1.91061 | 167.70 | 5.1862 | 77.80 |
| 1.91063 | 167.60 | 5.1988 | 77.70 |
| 1.91066 | 167.50 | 5.2114 | 77.60 |
| 1.91068 | 167.40 | 5.2240 | 77.50 |
| 1.91071 | 167.30 | 5.2367 | 77.40 |
| 1.91074 | 167.20 | 5.2494 | 77.30 |
| 1.91076 | 167.10 | 5.2621 | 77.20 |
| 1.91079 | 167.00 | 5.2748 | 77.10 |
| 1.91082 | 166.90 | 5.2875 | 77.00 |
| 1.91085 | 166.80 | 5.3003 | 76.90 |
| 1.91088 | 166.70 | 5.3131 | 76.80 |
| 1.91091 | 166.60 | 5.3260 | 76.70 |
| 1.91094 | 166.50 | 5.3388 | 76.60 |
| 1.91098 | 166.40 | 5.3517 | 76.50 |
| 1.91101 | 166.30 | 5.3646 | 76.40 |
| 1.91104 | 166.20 | 5.3776 | 76.30 |
| 1.91108 | 166.10 | 5.3906 | 76.20 |
| 1.91111 | 166.00 | 5.4036 | 76.10 |
| 1.91115 | 165.90 | 5.4166 | 76.00 |
| 1.91118 | 165.80 | 5.4296 | 75.90 |
| 1.91122 | 165.70 | 5.4427 | 75.80 |
| 1.91126 | 165.60 | 5.4558 | 75.70 |
| 1.91130 | 165.50 | 5.4690 | 75.60 |
| 1.91134 | 165.40 | 5.4821 | 75.50 |
| 1.91138 | 165.30 | 5.4953 | 75.40 |
| 1.91142 | 165.20 | 5.5085 | 75.30 |
| 1.91146 | 165.10 | 5.5218 | 75.20 |
| 1.91150 | 165.00 | 5.5350 | 75.10 |
| 1.91155 | 164.90 | 5.5483 | 75.00 |
| 1.91159 | 164.80 | 5.5617 | 74.90 |
| 1.91164 | 164.70 | 5.5750 | 74.80 |
| 1.91169 | 164.60 | 5.5884 | 74.70 |
| 1.91173 | 164.50 | 5.6018 | 74.60 |
| 1.91178 | 164.40 | 5.6153 | 74.50 |
| 1.91183 | 164.30 | 5.6287 | 74.40 |
| 1.91188 | 164.20 | 5.6422 | 74.30 |
| 1.91193 | 164.10 | 5.6558 | 74.20 |
| 1.91198 | 164.00 | 5.6693 | 74.10 |
| 1.91204 | 163.90 | 5.6829 | 74.00 |
| 1.91209 | 163.80 | 5.6965 | 73.90 |
| 1.91215 | 163.70 | 5.7102 | 73.80 |
| 1.91220 | 163.60 | 5.7239 | 73.70 |
| 1.91226 | 163.50 | 5.7376 | 73.60 |
| 1.91232 | 163.40 | 5.7513 | 73.50 |
| 1.91237 | 163.30 | 5.7651 | 73.40 |
| 1.91243 | 163.20 | 5.7789 | 73.30 |
| 1.91250 | 163.10 | 5.7927 | 73.20 |
| 1.91256 | 163.00 | 5.8065 | 73.10 |
| 1.91262 | 162.90 | 5.8204 | 73.00 |
| 1.91269 | 162.80 | 5.8343 | 72.90 |
| 1.91275 | 162.70 | 5.8483 | 72.80 |
| 1.91282 | 162.60 | 5.8623 | 72.70 |
| 1.91289 | 162.50 | 5.8763 | 72.60 |
| 1.91295 | 162.40 | 5.8903 | 72.50 |
| 1.91302 | 162.30 | 5.9044 | 72.40 |
| 1.91309 | 162.20 | 5.9185 | 72.30 |
| 1.91317 | 162.10 | 5.9326 | 72.20 |
| 1.91324 | 162.00 | 5.9468 | 72.10 |
| 1.91332 | 161.90 | 5.9610 | 72.00 |
| 1.91339 | 161.80 | 5.9752 | 71.90 |
| 1.91347 | 161.70 | 5.9895 | 71.80 |
| 1.91355 | 161.60 | 6.0038 | 71.70 |
| 1.91363 | 161.50 | 6.0181 | 71.60 |
| 1.91371 | 161.40 | 6.0325 | 71.50 |
| 1.91379 | 161.30 | 6.0468 | 71.40 |
| 1.91387 | 161.20 | 6.0613 | 71.30 |
| 1.91396 | 161.10 | 6.0757 | 71.20 |
| 1.91404 | 161.00 | 6.0902 | 71.10 |
| 1.9141 | 160.90 | 6.1047 | 71.00 |
| 1.9142 | 160.80 | 6.1193 | 70.90 |
| 1.9143 | 160.70 | 6.1339 | 70.80 |
| 1.9144 | 160.60 | 6.1485 | 70.70 |
| 1.9145 | 160.50 | 6.1631 | 70.60 |
| 1.9146 | 160.40 | 6.1778 | 70.50 |
| 1.9147 | 160.30 | 6.1925 | 70.40 |
| 1.9148 | 160.20 | 6.2073 | 70.30 |
| 1.9149 | 160.10 | 6.2221 | 70.20 |
| 1.9150 | 160.00 | 6.2369 | 70.10 |
| 1.9151 | 159.90 | 6.2518 | 70.00 |
| 1.9152 | 159.80 | 6.2667 | 69.90 |
| 1.9153 | 159.70 | 6.2816 | 69.80 |
| 1.9154 | 159.60 | 6.2965 | 69.70 |
| 1.9155 | 159.50 | 6.3115 | 69.60 |
| 1.9156 | 159.40 | 6.3266 | 69.50 |
| 1.9157 | 159.30 | 6.3416 | 69.40 |
| 1.9158 | 159.20 | 6.3567 | 69.30 |
| 1.9159 | 159.10 | 6.3719 | 69.20 |
| 1.9161 | 159.00 | 6.3870 | 69.10 |
| 1.9162 | 158.90 | 6.4023 | 69.00 |
| 1.9163 | 158.80 | 6.4175 | 68.90 |
| 1.9164 | 158.70 | 6.4328 | 68.80 |
| 1.9165 | 158.60 | 6.4481 | 68.70 |
| 1.9167 | 158.50 | 6.4634 | 68.60 |
| 1.9168 | 158.40 | 6.4788 | 68.50 |
| 1.9169 | 158.30 | 6.4943 | 68.40 |
| 1.9170 | 158.20 | 6.5097 | 68.30 |
| 1.9172 | 158.10 | 6.5252 | 68.20 |
| 1.9173 | 158.00 | 6.5408 | 68.10 |
| 1.9174 | 157.90 | 6.5563 | 68.00 |
| 1.9176 | 157.80 | 6.5719 | 67.90 |
| 1.9177 | 157.70 | 6.5876 | 67.80 |
| 1.9178 | 157.60 | 6.6033 | 67.70 |
| 1.9180 | 157.50 | 6.6190 | 67.60 |
| 1.9181 | 157.40 | 6.6348 | 67.50 |
| 1.9183 | 157.30 | 6.6506 | 67.40 |
| 1.9184 | 157.20 | 6.6664 | 67.30 |
| 1.9186 | 157.10 | 6.6823 | 67.20 |
| 1.9187 | 157.00 | 6.6982 | 67.10 |
| 1.9189 | 156.90 | 6.7141 | 67.00 |
| 1.9190 | 156.80 | 6.7301 | 66.90 |
| 1.9192 | 156.70 | 6.7462 | 66.80 |
| 1.9193 | 156.60 | 6.7622 | 66.70 |
| 1.9195 | 156.50 | 6.7784 | 66.60 |
| 1.9196 | 156.40 | 6.7945 | 66.50 |
| 1.9198 | 156.30 | 6.8107 | 66.40 |
| 1.9200 | 156.20 | 6.8269 | 66.30 |
| 1.9201 | 156.10 | 6.8432 | 66.20 |
| 1.9203 | 156.00 | 6.8595 | 66.10 |
| 1.9205 | 155.90 | 6.8759 | 66.00 |
| 1.9207 | 155.80 | 6.8923 | 65.90 |
| 1.9208 | 155.70 | 6.9087 | 65.80 |
| 1.9210 | 155.60 | 6.9252 | 65.70 |
| 1.9212 | 155.50 | 6.9417 | 65.60 |
| 1.9214 | 155.40 | 6.9583 | 65.50 |
| 1.9216 | 155.30 | 6.9749 | 65.40 |
| 1.9217 | 155.20 | 6.9915 | 65.30 |
| 1.9219 | 155.10 | 7.0082 | 65.20 |
| 1.9221 | 155.00 | 7.0249 | 65.10 |
| 1.9223 | 154.90 | 7.0417 | 65.00 |
| 1.9225 | 154.80 | 7.0585 | 64.90 |
| 1.9227 | 154.70 | 7.0754 | 64.80 |
| 1.9229 | 154.60 | 7.0923 | 64.70 |
| 1.9231 | 154.50 | 7.1092 | 64.60 |
| 1.9233 | 154.40 | 7.1262 | 64.50 |
| 1.9235 | 154.30 | 7.1432 | 64.40 |

TABLE 1-continued

| w3/v (unitless) | Θ Lookup (deg) | d3/v (unitless) | Θ Lookup (deg) |
|---|---|---|---|
| 1.9237 | 154.20 | 7.1603 | 64.30 |
| 1.9239 | 154.10 | 7.1774 | 64.20 |
| 1.9241 | 154.00 | 7.1946 | 64.10 |
| 1.9244 | 153.90 | 7.2118 | 64.00 |
| 1.9246 | 153.80 | 7.2290 | 63.90 |
| 1.9248 | 153.70 | 7.2463 | 63.80 |
| 1.9250 | 153.60 | 7.2637 | 63.70 |
| 1.9252 | 153.50 | 7.2811 | 63.60 |
| 1.9255 | 153.40 | 7.2985 | 63.50 |
| 1.9257 | 153.30 | 7.3160 | 63.40 |
| 1.9259 | 153.20 | 7.3335 | 63.30 |
| 1.9262 | 153.10 | 7.3511 | 63.20 |
| 1.9264 | 153.00 | 7.3687 | 63.10 |
| 1.9266 | 152.90 | 7.3864 | 63.00 |
| 1.9269 | 152.80 | 7.4041 | 62.90 |
| 1.9271 | 152.70 | 7.4218 | 62.80 |
| 1.9274 | 152.60 | 7.4396 | 62.70 |
| 1.9276 | 152.50 | 7.4575 | 62.60 |
| 1.9279 | 152.40 | 7.4754 | 62.50 |
| 1.9281 | 152.30 | 7.4933 | 62.40 |
| 1.9284 | 152.20 | 7.5113 | 62.30 |
| 1.9286 | 152.10 | 7.5294 | 62.20 |
| 1.9289 | 152.00 | 7.5475 | 62.10 |
| 1.9292 | 151.90 | 7.5656 | 62.00 |
| 1.9294 | 151.80 | 7.5838 | 61.90 |
| 1.9297 | 151.70 | 7.6021 | 61.80 |
| 1.9300 | 151.60 | 7.6204 | 61.70 |
| 1.9303 | 151.50 | 7.6387 | 61.60 |
| 1.9305 | 151.40 | 7.6571 | 61.50 |
| 1.9308 | 151.30 | 7.6755 | 61.40 |
| 1.9311 | 151.20 | 7.6940 | 61.30 |
| 1.9314 | 151.10 | 7.7126 | 61.20 |
| 1.9317 | 151.00 | 7.7312 | 61.10 |
| 1.9320 | 150.90 | 7.7498 | 61.00 |
| 1.9323 | 150.80 | 7.7685 | 60.90 |
| 1.9326 | 150.70 | 7.7872 | 60.80 |
| 1.9329 | 150.60 | 7.8060 | 60.70 |
| 1.9332 | 150.50 | 7.8249 | 60.60 |
| 1.9335 | 150.40 | 7.8438 | 60.50 |
| 1.9338 | 150.30 | 7.8628 | 60.40 |
| 1.9341 | 150.20 | 7.8818 | 60.30 |
| 1.9344 | 150.10 | 7.9008 | 60.20 |
| 1.9347 | 150.00 | 7.9200 | 60.10 |
| 1.9351 | 149.90 | 7.9391 | 60.00 |
| 1.9354 | 149.80 | 7.9584 | 59.90 |
| 1.9357 | 149.70 | 7.9776 | 59.80 |
| 1.9360 | 149.60 | 7.9970 | 59.70 |
| 1.9364 | 149.50 | 8.0164 | 59.60 |
| 1.9367 | 149.40 | 8.0358 | 59.50 |
| 1.9371 | 149.30 | 8.0553 | 59.40 |
| 1.9374 | 149.20 | 8.0749 | 59.30 |
| 1.9378 | 149.10 | 8.0945 | 59.20 |
| 1.9381 | 149.00 | 8.1142 | 59.10 |
| 1.9385 | 148.90 | 8.1339 | 59.00 |
| 1.9388 | 148.80 | 8.1537 | 58.90 |
| 1.9392 | 148.70 | 8.1735 | 58.80 |
| 1.9395 | 148.60 | 8.1934 | 58.70 |
| 1.9399 | 148.50 | 8.2134 | 58.60 |
| 1.9403 | 148.40 | 8.2334 | 58.50 |
| 1.9406 | 148.30 | 8.2535 | 58.40 |
| 1.9410 | 148.20 | 8.2736 | 58.30 |
| 1.9414 | 148.10 | 8.2938 | 58.20 |
| 1.9418 | 148.00 | 8.3140 | 58.10 |
| 1.9422 | 147.90 | 8.3343 | 58.00 |
| 1.9426 | 147.80 | 8.3547 | 57.90 |
| 1.9430 | 147.70 | 8.3751 | 57.80 |
| 1.9433 | 147.60 | 8.3956 | 57.70 |
| 1.9437 | 147.50 | 8.4162 | 57.60 |
| 1.9442 | 147.40 | 8.4368 | 57.50 |
| 1.9446 | 147.30 | 8.4575 | 57.40 |
| 1.9450 | 147.20 | 8.4782 | 57.30 |
| 1.9454 | 147.10 | 8.4990 | 57.20 |
| 1.9458 | 147.00 | 8.5199 | 57.10 |
| 1.9462 | 146.90 | 8.5408 | 57.00 |
| 1.9466 | 146.80 | 8.5618 | 56.90 |
| 1.9471 | 146.70 | 8.5828 | 56.80 |
| 1.9475 | 146.60 | 8.6039 | 56.70 |
| 1.9479 | 146.50 | 8.6251 | 56.60 |
| 1.9484 | 146.40 | 8.6464 | 56.50 |
| 1.9488 | 146.30 | 8.6677 | 56.40 |
| 1.9493 | 146.20 | 8.6890 | 56.30 |
| 1.9497 | 146.10 | 8.7105 | 56.20 |
| 1.9502 | 146.00 | 8.7320 | 56.10 |
| 1.9506 | 145.90 | 8.7535 | 56.00 |
| 1.9511 | 145.80 | 8.7752 | 55.90 |
| 1.9516 | 145.70 | 8.7969 | 55.80 |
| 1.9520 | 145.60 | 8.8187 | 55.70 |
| 1.9525 | 145.50 | 8.8405 | 55.60 |
| 1.9530 | 145.40 | 8.8624 | 55.50 |
| 1.9535 | 145.30 | 8.8844 | 55.40 |
| 1.9539 | 145.20 | 8.9064 | 55.30 |
| 1.9544 | 145.10 | 8.9285 | 55.20 |
| 1.9549 | 145.00 | 8.9507 | 55.10 |
| 1.9554 | 144.90 | 8.9730 | 55.00 |
| 1.9559 | 144.80 | 8.9953 | 54.90 |
| 1.9564 | 144.70 | 9.0177 | 54.80 |
| 1.9569 | 144.60 | 9.0401 | 54.70 |
| 1.9574 | 144.50 | 9.0627 | 54.60 |
| 1.9580 | 144.40 | 9.0853 | 54.50 |
| 1.9585 | 144.30 | 9.1079 | 54.40 |
| 1.9590 | 144.20 | 9.1307 | 54.30 |
| 1.9595 | 144.10 | 9.1535 | 54.20 |
| 1.9601 | 144.00 | 9.1764 | 54.10 |
| 1.9606 | 143.90 | 9.1994 | 54.00 |
| 1.9611 | 143.80 | 9.2224 | 53.90 |
| 1.9617 | 143.70 | 9.2456 | 53.80 |
| 1.9622 | 143.60 | 9.2687 | 53.70 |
| 1.9628 | 143.50 | 9.2920 | 53.60 |
| 1.9633 | 143.40 | 9.3154 | 53.50 |
| 1.9639 | 143.30 | 9.3388 | 53.40 |
| 1.9645 | 143.20 | 9.3623 | 53.30 |
| 1.9650 | 143.10 | 9.3859 | 53.20 |
| 1.9656 | 143.00 | 9.4095 | 53.10 |
| 1.9662 | 142.90 | 9.4332 | 53.00 |
| 1.9668 | 142.80 | 9.4571 | 52.90 |
| 1.9674 | 142.70 | 9.4809 | 52.80 |
| 1.9680 | 142.60 | 9.5049 | 52.70 |
| 1.9686 | 142.50 | 9.5290 | 52.60 |
| 1.9692 | 142.40 | 9.5531 | 52.50 |
| 1.9698 | 142.30 | 9.5773 | 52.40 |
| 1.9704 | 142.20 | 9.6016 | 52.30 |
| 1.9710 | 142.10 | 9.6260 | 52.20 |
| 1.9716 | 142.00 | 9.6504 | 52.10 |
| 1.9722 | 141.90 | 9.6749 | 52.00 |
| 1.9729 | 141.80 | 9.6996 | 51.90 |
| 1.9735 | 141.70 | 9.7243 | 51.80 |
| 1.9741 | 141.60 | 9.7491 | 51.70 |
| 1.9748 | 141.50 | 9.7739 | 51.60 |
| 1.9754 | 141.40 | 9.7989 | 51.50 |
| 1.9761 | 141.30 | 9.8239 | 51.40 |
| 1.9767 | 141.20 | 9.8490 | 51.30 |
| 1.9774 | 141.10 | 9.8743 | 51.20 |
| 1.9781 | 141.00 | 9.8996 | 51.10 |
| 1.9787 | 140.90 | 9.9249 | 51.00 |
| 1.9794 | 140.80 | 9.9504 | 50.90 |
| 1.9801 | 140.70 | 9.9760 | 50.80 |
| 1.9808 | 140.60 | 10.0016 | 50.70 |
| 1.9815 | 140.50 | 10.0274 | 50.60 |
| 1.9822 | 140.40 | 10.0532 | 50.50 |
| 1.9829 | 140.30 | 10.0791 | 50.40 |
| 1.9836 | 140.20 | 10.1052 | 50.30 |
| 1.9843 | 140.10 | 10.1313 | 50.20 |
| 1.9850 | 140.00 | 10.1575 | 50.10 |
| 1.9857 | 139.90 | 10.1838 | 50.00 |
| 1.9864 | 139.80 | 10.2101 | 49.90 |
| 1.9872 | 139.70 | 10.2366 | 49.80 |
| 1.9879 | 139.60 | 10.2632 | 49.70 |
| 1.9886 | 139.50 | 10.2899 | 49.60 |
| 1.9894 | 139.40 | 10.3166 | 49.50 |
| 1.9901 | 139.30 | 10.3435 | 49.40 |
| 1.9909 | 139.20 | 10.3704 | 49.30 |
| 1.9917 | 139.10 | 10.3975 | 49.20 |
| 1.9924 | 139.00 | 10.4247 | 49.10 |
| 1.9932 | 138.90 | 10.4519 | 49.00 |
| 1.9940 | 138.80 | 10.4793 | 48.90 |
| 1.9947 | 138.70 | 10.5067 | 48.80 |

TABLE 1-continued

| w3/v (unitless) | Θ Lookup (deg) | d3/v (unitless) | Θ Lookup (deg) |
| --- | --- | --- | --- |
| 1.9955 | 138.60 | 10.5343 | 48.70 |
| 1.9963 | 138.50 | 10.5619 | 48.60 |
| 1.9971 | 138.40 | 10.5897 | 48.50 |
| 1.9979 | 138.30 | 10.6175 | 48.40 |
| 1.9987 | 138.20 | 10.6455 | 48.30 |
| 1.9995 | 138.10 | 10.6735 | 48.20 |
| 2.0004 | 138.00 | 10.7017 | 48.10 |
| 2.0012 | 137.90 | 10.7300 | 48.00 |
| 2.0020 | 137.80 | 10.7584 | 47.90 |
| 2.0029 | 137.70 | 10.7868 | 47.80 |
| 2.0037 | 137.60 | 10.8154 | 47.70 |
| 2.0045 | 137.50 | 10.8441 | 47.60 |
| 2.0054 | 137.40 | 10.8729 | 47.50 |
| 2.0063 | 137.30 | 10.9018 | 47.40 |
| 2.0071 | 137.20 | 10.9309 | 47.30 |
| 2.0080 | 137.10 | 10.9600 | 47.20 |
| 2.0089 | 137.00 | 10.9892 | 47.10 |
| 2.0097 | 136.90 | 11.0186 | 47.00 |
| 2.0106 | 136.80 | 11.0481 | 46.90 |
| 2.0115 | 136.70 | 11.0777 | 46.80 |
| 2.0124 | 136.60 | 11.1074 | 46.70 |
| 2.0133 | 136.50 | 11.1372 | 46.60 |
| 2.0142 | 136.40 | 11.1671 | 46.50 |
| 2.0151 | 136.30 | 11.1971 | 46.40 |
| 2.0161 | 136.20 | 11.2273 | 46.30 |
| 2.0170 | 136.10 | 11.2576 | 46.20 |
| 2.0179 | 136.00 | 11.2880 | 46.10 |
| 2.0189 | 135.90 | 11.3185 | 46.00 |
| 2.0198 | 135.80 | 11.3491 | 45.90 |
| 2.0208 | 135.70 | 11.3799 | 45.80 |
| 2.0217 | 135.60 | 11.4107 | 45.70 |
| 2.0227 | 135.50 | 11.4417 | 45.60 |
| 2.0236 | 135.40 | 11.4729 | 45.50 |
| 2.0246 | 135.30 | 11.5041 | 45.40 |
| 2.0256 | 135.20 | 11.5355 | 45.30 |
| 2.0266 | 135.10 | 11.5670 | 45.20 |
| 2.0276 | 135.00 | 11.5986 | 45.10 |
| 2.0286 | 134.90 | 11.6303 | 45.00 |
| 2.0296 | 134.80 | 11.6622 | 44.90 |
| 2.0306 | 134.70 | 11.6942 | 44.80 |
| 2.0316 | 134.60 | 11.7264 | 44.70 |
| 2.0326 | 134.50 | 11.7586 | 44.60 |
| 2.0337 | 134.40 | 11.7910 | 44.50 |
| 2.0347 | 134.30 | 11.8236 | 44.40 |
| 2.0357 | 134.20 | 11.8562 | 44.30 |
| 2.0368 | 134.10 | 11.8890 | 44.20 |
| 2.0379 | 134.00 | 11.9219 | 44.10 |
| 2.0389 | 133.90 | 11.9550 | 44.00 |
| 2.0400 | 133.80 | 11.9882 | 43.90 |
| 2.0411 | 133.70 | 12.0216 | 43.80 |
| 2.0421 | 133.60 | 12.0550 | 43.70 |
| 2.0432 | 133.50 | 12.0887 | 43.60 |
| 2.0443 | 133.40 | 12.1224 | 43.50 |
| 2.0454 | 133.30 | 12.1563 | 43.40 |
| 2.0465 | 133.20 | 12.1904 | 43.30 |
| 2.0477 | 133.10 | 12.2246 | 43.20 |
| 2.0488 | 133.00 | 12.2589 | 43.10 |
| 2.0499 | 132.90 | 12.2934 | 43.00 |
| 2.0510 | 132.80 | 12.3280 | 42.90 |
| 2.0522 | 132.70 | 12.3628 | 42.80 |
| 2.0533 | 132.60 | 12.3977 | 42.70 |
| 2.0545 | 132.50 | 12.4328 | 42.60 |
| 2.0556 | 132.40 | 12.4680 | 42.50 |
| 2.0568 | 132.30 | 12.5034 | 42.40 |
| 2.0580 | 132.20 | 12.5389 | 42.30 |
| 2.0592 | 132.10 | 12.5746 | 42.20 |
| 2.0604 | 132.00 | 12.6105 | 42.10 |
| 2.0616 | 131.90 | 12.6465 | 42.00 |
| 2.0628 | 131.80 | 12.6826 | 41.90 |
| 2.0640 | 131.70 | 12.7189 | 41.80 |
| 2.0652 | 131.60 | 12.7554 | 41.70 |
| 2.0664 | 131.50 | 12.7920 | 41.60 |
| 2.0677 | 131.40 | 12.8288 | 41.50 |
| 2.0689 | 131.30 | 12.8658 | 41.40 |
| 2.0702 | 131.20 | 12.9029 | 41.30 |
| 2.0714 | 131.10 | 12.9402 | 41.20 |
| 2.0727 | 131.00 | 12.9776 | 41.10 |
| 2.0739 | 130.90 | 13.0153 | 41.00 |

TABLE 1-continued

| w3/v (unitless) | Θ Lookup (deg) | d3/v (unitless) | Θ Lookup (deg) |
| --- | --- | --- | --- |
| 2.0752 | 130.80 | 13.0531 | 40.90 |
| 2.0765 | 130.70 | 13.0910 | 40.80 |
| 2.0778 | 130.60 | 13.1292 | 40.70 |
| 2.0791 | 130.50 | 13.1675 | 40.60 |
| 2.0804 | 130.40 | 13.2060 | 40.50 |
| 2.0817 | 130.30 | 13.2446 | 40.40 |
| 2.0830 | 130.20 | 13.2834 | 40.30 |
| 2.0844 | 130.10 | 13.3225 | 40.20 |
| 2.0857 | 130.00 | 13.3616 | 40.10 |
| 2.0870 | 129.90 | 13.4010 | 40.00 |
| 2.0884 | 129.80 | 13.4406 | 39.90 |
| 2.0897 | 129.70 | 13.4803 | 39.80 |
| 2.0911 | 129.60 | 13.5202 | 39.70 |
| 2.0925 | 129.50 | 13.5604 | 39.60 |
| 2.0939 | 129.40 | 13.6007 | 39.50 |
| 2.0953 | 129.30 | 13.6411 | 39.40 |
| 2.0967 | 129.20 | 13.6818 | 39.30 |
| 2.0981 | 129.10 | 13.7227 | 39.20 |
| 2.0995 | 129.00 | 13.7638 | 39.10 |
| 2.1009 | 128.90 | 13.8050 | 39.00 |
| 2.1023 | 128.80 | 13.8465 | 38.90 |
| 2.1038 | 128.70 | 13.8881 | 38.80 |
| 2.1052 | 128.60 | 13.9300 | 38.70 |
| 2.1067 | 128.50 | 13.9720 | 38.60 |
| 2.1081 | 128.40 | 14.0143 | 38.50 |
| 2.1096 | 128.30 | 14.0568 | 38.40 |
| 2.1111 | 128.20 | 14.0994 | 38.30 |
| 2.1126 | 128.10 | 14.1423 | 38.20 |
| 2.1141 | 128.00 | 14.1854 | 38.10 |
| 2.1156 | 127.90 | 14.2287 | 38.00 |
| 2.1171 | 127.80 | 14.2722 | 37.90 |
| 2.1186 | 127.70 | 14.3159 | 37.80 |
| 2.1201 | 127.60 | 14.3599 | 37.70 |
| 2.1217 | 127.50 | 14.4040 | 37.60 |
| 2.1232 | 127.40 | 14.4484 | 37.50 |
| 2.1248 | 127.30 | 14.4930 | 37.40 |
| 2.1263 | 127.20 | 14.5378 | 37.30 |
| 2.1279 | 127.10 | 14.5829 | 37.20 |
| 2.1295 | 127.00 | 14.6282 | 37.10 |
| 2.1311 | 126.90 | 14.6737 | 37.00 |
| 2.1327 | 126.80 | 14.7194 | 36.90 |
| 2.1343 | 126.70 | 14.7654 | 36.80 |
| 2.1359 | 126.60 | 14.8116 | 36.70 |
| 2.1375 | 126.50 | 14.8580 | 36.60 |
| 2.1391 | 126.40 | 14.9047 | 36.50 |
| 2.1408 | 126.30 | 14.9516 | 36.40 |
| 2.1424 | 126.20 | 14.9987 | 36.30 |
| 2.1441 | 126.10 | 15.0461 | 36.20 |
| 2.1457 | 126.00 | 15.0938 | 36.10 |
| 2.1474 | 125.90 | 15.1417 | 36.00 |
| 2.1491 | 125.80 | 15.1898 | 35.90 |
| 2.1508 | 125.70 | 15.2382 | 35.80 |
| 2.1525 | 125.60 | 15.2869 | 35.70 |
| 2.1542 | 125.50 | 15.3358 | 35.60 |
| 2.1559 | 125.40 | 15.3849 | 35.50 |
| 2.1577 | 125.30 | 15.4343 | 35.40 |
| 2.1594 | 125.20 | 15.4840 | 35.30 |
| 2.1611 | 125.10 | 15.5340 | 35.20 |
| 2.1629 | 125.00 | 15.5842 | 35.10 |
| 2.1647 | 124.90 | 15.6347 | 35.00 |
| 2.1664 | 124.80 | 15.6855 | 34.90 |
| 2.1682 | 124.70 | 15.7365 | 34.80 |
| 2.1700 | 124.60 | 15.7878 | 34.70 |
| 2.1718 | 124.50 | 15.8394 | 34.60 |
| 2.1736 | 124.40 | 15.8913 | 34.50 |
| 2.1755 | 124.30 | 15.9434 | 34.40 |
| 2.1773 | 124.20 | 15.9959 | 34.30 |
| 2.1791 | 124.10 | 16.0486 | 34.20 |
| 2.1810 | 124.00 | 16.1017 | 34.10 |
| 2.1829 | 123.90 | 16.1550 | 34.00 |
| 2.1847 | 123.80 | 16.2086 | 33.90 |
| 2.1866 | 123.70 | 16.2625 | 33.80 |
| 2.1885 | 123.60 | 16.3167 | 33.70 |
| 2.1904 | 123.50 | 16.3713 | 33.60 |
| 2.1923 | 123.40 | 16.4261 | 33.50 |
| 2.1942 | 123.30 | 16.4812 | 33.40 |
| 2.1962 | 123.20 | 16.5367 | 33.30 |
| 2.1981 | 123.10 | 16.5925 | 33.20 |

TABLE 1-continued

| w3/v (unitless) | Θ Lookup (deg) | d3/v (unitless) | Θ Lookup (deg) |
| --- | --- | --- | --- |
| 2.2001 | 123.00 | 16.6485 | 33.10 |
| 2.2020 | 122.90 | 16.7050 | 33.00 |
| 2.2040 | 122.80 | 16.7617 | 32.90 |
| 2.2060 | 122.70 | 16.8188 | 32.80 |
| 2.2080 | 122.60 | 16.8762 | 32.70 |
| 2.2100 | 122.50 | 16.9339 | 32.60 |
| 2.2120 | 122.40 | 16.9920 | 32.50 |
| 2.2140 | 122.30 | 17.0504 | 32.40 |
| 2.2161 | 122.20 | 17.1091 | 32.30 |
| 2.2181 | 122.10 | 17.1682 | 32.20 |
| 2.2202 | 122.00 | 17.2276 | 32.10 |
| 2.2222 | 121.90 | 17.2874 | 32.00 |
| 2.2243 | 121.80 | 17.3476 | 31.90 |
| 2.2264 | 121.70 | 17.4081 | 31.80 |
| 2.2285 | 121.60 | 17.4690 | 31.70 |
| 2.2306 | 121.50 | 17.5302 | 31.60 |
| 2.2327 | 121.40 | 17.5918 | 31.50 |
| 2.2348 | 121.30 | 17.6538 | 31.40 |
| 2.2370 | 121.20 | 17.7162 | 31.30 |
| 2.2391 | 121.10 | 17.7789 | 31.20 |
| 2.2413 | 121.00 | 17.8421 | 31.10 |
| 2.2435 | 120.90 | 17.9056 | 31.00 |
| 2.2457 | 120.80 | 17.9695 | 30.90 |
| 2.2478 | 120.70 | 18.0338 | 30.80 |
| 2.2501 | 120.60 | 18.0985 | 30.70 |
| 2.2523 | 120.50 | 18.1636 | 30.60 |
| 2.2545 | 120.40 | 18.2291 | 30.50 |
| 2.2567 | 120.30 | 18.2950 | 30.40 |
| 2.2590 | 120.20 | 18.3614 | 30.30 |
| 2.2613 | 120.10 | 18.4281 | 30.20 |
| 2.2635 | 120.00 | 18.4953 | 30.10 |
| 2.2658 | 119.90 | 18.5629 | 30.00 |
| 2.2681 | 119.80 | 18.6310 | 29.90 |
| 2.2704 | 119.70 | 18.6994 | 29.80 |
| 2.2728 | 119.60 | 18.7684 | 29.70 |
| 2.2751 | 119.50 | 18.8377 | 29.60 |
| 2.2774 | 119.40 | 18.9075 | 29.50 |
| 2.2798 | 119.30 | 18.9778 | 29.40 |
| 2.2822 | 119.20 | 19.0485 | 29.30 |
| 2.2845 | 119.10 | 19.1197 | 29.20 |
| 2.2869 | 119.00 | 19.1914 | 29.10 |
| 2.2893 | 118.90 | 19.2635 | 29.00 |
| 2.2917 | 118.80 | 19.3362 | 28.90 |
| 2.2942 | 118.70 | 19.4093 | 28.80 |
| 2.2966 | 118.60 | 19.4828 | 28.70 |
| 2.2991 | 118.50 | 19.5569 | 28.60 |
| 2.3015 | 118.40 | 19.6315 | 28.50 |
| 2.3040 | 118.30 | 19.7066 | 28.40 |
| 2.3065 | 118.20 | 19.7822 | 28.30 |
| 2.3090 | 118.10 | 19.8583 | 28.20 |
| 2.3115 | 118.00 | 19.9349 | 28.10 |
| 2.3140 | 117.90 | 20.0121 | 28.00 |
| 2.3166 | 117.80 | 20.0897 | 27.90 |
| 2.3191 | 117.70 | 20.1680 | 27.80 |
| 2.3217 | 117.60 | 20.2467 | 27.70 |
| 2.3243 | 117.50 | 20.3260 | 27.60 |
| 2.3269 | 117.40 | 20.4059 | 27.50 |
| 2.3295 | 117.30 | 20.4863 | 27.40 |
| 2.3321 | 117.20 | 20.5673 | 27.30 |
| 2.3347 | 117.10 | 20.6489 | 27.20 |
| 2.3374 | 117.00 | 20.7311 | 27.10 |
| 2.3400 | 116.90 | 20.8138 | 27.00 |
| 2.3427 | 116.80 | 20.8971 | 26.90 |
| 2.3454 | 116.70 | 20.9811 | 26.80 |
| 2.3481 | 116.60 | 21.0656 | 26.70 |
| 2.3508 | 116.50 | 21.1508 | 26.60 |
| 2.3535 | 116.40 | 21.2365 | 26.50 |
| 2.3562 | 116.30 | 21.3229 | 26.40 |
| 2.3590 | 116.20 | 21.4100 | 26.30 |
| 2.3617 | 116.10 | 21.4976 | 26.20 |
| 2.3645 | 116.00 | 21.5860 | 26.10 |
| 2.3673 | 115.90 | 21.6749 | 26.00 |
| 2.3701 | 115.80 | 21.7646 | 25.90 |
| 2.3729 | 115.70 | 21.8549 | 25.80 |
| 2.3758 | 115.60 | 21.9459 | 25.70 |
| 2.3786 | 115.50 | 22.0376 | 25.60 |
| 2.3815 | 115.40 | 22.1299 | 25.50 |
| 2.3843 | 115.30 | 22.2230 | 25.40 |
| 2.3872 | 115.20 | 22.3168 | 25.30 |
| 2.3901 | 115.10 | 22.4113 | 25.20 |
| 2.3930 | 115.00 | 22.5066 | 25.10 |
| 2.3960 | 114.90 | 22.6026 | 25.00 |
| 2.3989 | 114.80 | 22.6993 | 24.90 |
| 2.4019 | 114.70 | 22.7968 | 24.80 |
| 2.4048 | 114.60 | 22.8950 | 24.70 |
| 2.4078 | 114.50 | 22.9940 | 24.60 |
| 2.4108 | 114.40 | 23.0938 | 24.50 |
| 2.4138 | 114.30 | 23.1945 | 24.40 |
| 2.4169 | 114.20 | 23.2959 | 24.30 |
| 2.4199 | 114.10 | 23.3981 | 24.20 |
| 2.4230 | 114.00 | 23.5011 | 24.10 |
| 2.4260 | 113.90 | 23.6050 | 24.00 |
| 2.4291 | 113.80 | 23.7097 | 23.90 |
| 2.4322 | 113.70 | 23.8153 | 23.80 |
| 2.4354 | 113.60 | 23.9217 | 23.70 |
| 2.4385 | 113.50 | 24.0290 | 23.60 |
| 2.4416 | 113.40 | 24.1372 | 23.50 |
| 2.4448 | 113.30 | 24.2464 | 23.40 |
| 2.4480 | 113.20 | 24.3564 | 23.30 |
| 2.4512 | 113.10 | 24.4673 | 23.20 |
| 2.4544 | 113.00 | 24.5792 | 23.10 |
| 2.4576 | 112.90 | 24.6920 | 23.00 |
| 2.4609 | 112.80 | 24.8058 | 22.90 |
| 2.4641 | 112.70 | 24.9205 | 22.80 |
| 2.4674 | 112.60 | 25.0363 | 22.70 |
| 2.4707 | 112.50 | 25.1530 | 22.60 |
| 2.4740 | 112.40 | 25.2707 | 22.50 |
| 2.4773 | 112.30 | 25.3895 | 22.40 |
| 2.4807 | 112.20 | 25.5093 | 22.30 |
| 2.4840 | 112.10 | 25.6302 | 22.20 |
| 2.4874 | 112.00 | 25.7521 | 22.10 |
| 2.4908 | 111.90 | 25.8751 | 22.00 |
| 2.4942 | 111.80 | 25.9992 | 21.90 |
| 2.4976 | 111.70 | 26.1244 | 21.80 |
| 2.5011 | 111.60 | 26.2508 | 21.70 |
| 2.5045 | 111.50 | 26.3783 | 21.60 |
| 2.5080 | 111.40 | 26.5069 | 21.50 |
| 2.5115 | 111.30 | 26.6367 | 21.40 |
| 2.5150 | 111.20 | 26.7677 | 21.30 |
| 2.5185 | 111.10 | 26.8999 | 21.20 |
| 2.5220 | 111.00 | 27.0334 | 21.10 |
| 2.5256 | 110.90 | 27.1681 | 21.00 |
| 2.5292 | 110.80 | 27.3040 | 20.90 |
| 2.5328 | 110.70 | 27.4412 | 20.80 |
| 2.5364 | 110.60 | 27.5797 | 20.70 |
| 2.5400 | 110.50 | 27.7196 | 20.60 |
| 2.5436 | 110.40 | 27.8608 | 20.50 |
| 2.5473 | 110.30 | 28.0033 | 20.40 |
| 2.5510 | 110.20 | 28.1472 | 20.30 |
| 2.5547 | 110.10 | 28.2925 | 20.20 |
| 2.5584 | 110.00 | 28.4392 | 20.10 |
| 2.5621 | 109.90 | 28.5873 | 20.00 |
| 2.5659 | 109.80 | 28.7369 | 19.90 |
| 2.5696 | 109.70 | 28.8880 | 19.80 |
| 2.5734 | 109.60 | 29.0406 | 19.70 |
| 2.5772 | 109.50 | 29.1947 | 19.60 |
| 2.5810 | 109.40 | 29.3504 | 19.50 |
| 2.5849 | 109.30 | 29.5076 | 19.40 |
| 2.5887 | 109.20 | 29.6665 | 19.30 |
| 2.5926 | 109.10 | 29.8270 | 19.20 |
| 2.5965 | 109.00 | 29.9891 | 19.10 |
| 2.6004 | 108.90 | 30.1529 | 19.00 |
| 2.6044 | 108.80 | 30.3183 | 18.90 |
| 2.6083 | 108.70 | 30.4856 | 18.80 |
| 2.6123 | 108.60 | 30.6545 | 18.70 |
| 2.6163 | 108.50 | 30.8253 | 18.60 |
| 2.6203 | 108.40 | 30.9979 | 18.50 |
| 2.6243 | 108.30 | 31.1723 | 18.40 |
| 2.6284 | 108.20 | 31.3486 | 18.30 |
| 2.6324 | 108.10 | 31.5268 | 18.20 |
| 2.6365 | 108.00 | 31.7069 | 18.10 |
| 2.6406 | 107.90 | 31.8890 | 18.00 |
| 2.6448 | 107.80 | 32.0731 | 17.90 |
| 2.6489 | 107.70 | 32.2593 | 17.80 |
| 2.6531 | 107.60 | 32.4475 | 17.70 |
| 2.6573 | 107.50 | 32.6378 | 17.60 |

TABLE 1-continued

| w3/v (unitless) | Θ Lookup (deg) | d3/v (unitless) | Θ Lookup (deg) | w3/v (unitless) | Θ Lookup (deg) | d3/v (unitless) | Θ Lookup (deg) |
|---|---|---|---|---|---|---|---|
| 2.6615 | 107.40 | 32.8302 | 17.50 | 3.0611 | 99.60 | 59.8785 | 9.70 |
| 2.6657 | 107.30 | 33.0249 | 17.40 | 3.0673 | 99.50 | 60.5082 | 9.60 |
| 2.6699 | 107.20 | 33.2217 | 17.30 | 3.0735 | 99.40 | 61.1511 | 9.50 |
| 2.6742 | 107.10 | 33.4208 | 17.20 | 3.0797 | 99.30 | 61.8076 | 9.40 |
| 2.6785 | 107.00 | 33.6222 | 17.10 | 3.0859 | 99.20 | 62.4781 | 9.30 |
| 2.6828 | 106.90 | 33.8259 | 17.00 | 3.0922 | 99.10 | 63.1632 | 9.20 |
| 2.6872 | 106.80 | 34.0320 | 16.90 | 3.0986 | 99.00 | 63.8633 | 9.10 |
| 2.6915 | 106.70 | 34.2406 | 16.80 | 3.1049 | 98.90 | 64.5788 | 9.00 |
| 2.6959 | 106.60 | 34.4516 | 16.70 | 3.1113 | 98.80 | 65.3104 | 8.90 |
| 2.7003 | 106.50 | 34.6650 | 16.60 | 3.1177 | 98.70 | 66.0585 | 8.80 |
| 2.7047 | 106.40 | 34.8811 | 16.50 | 3.1242 | 98.60 | 66.8238 | 8.70 |
| 2.7091 | 106.30 | 35.0997 | 16.40 | 3.1307 | 98.50 | 67.6068 | 8.60 |
| 2.7136 | 106.20 | 35.3210 | 16.30 | 3.1372 | 98.40 | 68.4081 | 8.50 |
| 2.7181 | 106.10 | 35.5450 | 16.20 | 3.1437 | 98.30 | 69.2284 | 8.40 |
| 2.7226 | 106.00 | 35.7717 | 16.10 | 3.1503 | 98.20 | 70.0685 | 8.30 |
| 2.7271 | 105.90 | 36.0013 | 16.00 | 3.1569 | 98.10 | 70.9289 | 8.20 |
| 2.7316 | 105.80 | 36.2336 | 15.90 | 3.1636 | 98.00 | 71.8106 | 8.10 |
| 2.7362 | 105.70 | 36.4689 | 15.80 | 3.1702 | 97.90 | 72.7142 | 8.00 |
| 2.7408 | 105.60 | 36.7071 | 15.70 | 3.1769 | 97.80 | 73.6406 | 7.90 |
| 2.7454 | 105.50 | 36.9484 | 15.60 | 3.1837 | 97.70 | 74.5907 | 7.80 |
| 2.7500 | 105.40 | 37.1927 | 15.50 | 3.1905 | 97.60 | 75.5653 | 7.70 |
| 2.7547 | 105.30 | 37.4402 | 15.40 | 3.1973 | 97.50 | 76.5656 | 7.60 |
| 2.7594 | 105.20 | 37.6908 | 15.30 | 3.2041 | 97.40 | 77.5924 | 7.50 |
| 2.7641 | 105.10 | 37.9448 | 15.20 | 3.2110 | 97.30 | 78.6469 | 7.40 |
| 2.7688 | 105.00 | 38.2020 | 15.10 | 3.2179 | 97.20 | 79.7303 | 7.30 |
| 2.7735 | 104.90 | 38.4626 | 15.00 | 3.2249 | 97.10 | 80.8436 | 7.20 |
| 2.7783 | 104.80 | 38.7267 | 14.90 | 3.2318 | 97.00 | 81.9882 | 7.10 |
| 2.7831 | 104.70 | 38.9944 | 14.80 | 3.2389 | 96.90 | 83.1654 | 7.00 |
| 2.7879 | 104.60 | 39.2656 | 14.70 | 3.2459 | 96.80 | 84.3767 | 6.90 |
| 2.7928 | 104.50 | 39.5405 | 14.60 | 3.2530 | 96.70 | 85.6235 | 6.80 |
| 2.7976 | 104.40 | 39.8191 | 14.50 | 3.2601 | 96.60 | 86.9074 | 6.70 |
| 2.8025 | 104.30 | 40.1016 | 14.40 | 3.2673 | 96.50 | 88.2302 | 6.60 |
| 2.8074 | 104.20 | 40.3880 | 14.30 | 3.2745 | 96.40 | 89.5935 | 6.50 |
| 2.8124 | 104.10 | 40.6783 | 14.20 | 3.2817 | 96.30 | 90.9994 | 6.40 |
| 2.8173 | 104.00 | 40.9728 | 14.10 | 3.2890 | 96.20 | 92.4498 | 6.30 |
| 2.8223 | 103.90 | 41.2714 | 14.00 | 3.2963 | 96.10 | 93.9469 | 6.20 |
| 2.8273 | 103.80 | 41.5743 | 13.90 | 3.3036 | 96.00 | 95.4930 | 6.10 |
| 2.8323 | 103.70 | 41.8815 | 13.80 | 3.3110 | 95.90 | 97.0905 | 6.00 |
| 2.8374 | 103.60 | 42.1932 | 13.70 | 3.3184 | 95.80 | 98.7421 | 5.90 |
| 2.8425 | 103.50 | 42.5094 | 13.60 | 3.3259 | 95.70 | 100.4506 | 5.80 |
| 2.8476 | 103.40 | 42.8302 | 13.50 | 3.3334 | 95.60 | 102.2188 | 5.70 |
| 2.8527 | 103.30 | 43.1558 | 13.40 | 3.3409 | 95.50 | 104.0501 | 5.60 |
| 2.8578 | 103.20 | 43.4862 | 13.30 | 3.3484 | 95.40 | 105.9479 | 5.50 |
| 2.8630 | 103.10 | 43.8216 | 13.20 | 3.3560 | 95.30 | 107.9159 | 5.40 |
| 2.8682 | 103.00 | 44.1621 | 13.10 | 3.3637 | 95.20 | 109.9580 | 5.30 |
| 2.8735 | 102.90 | 44.5077 | 13.00 | 3.3714 | 95.10 | 112.0786 | 5.20 |
| 2.8787 | 102.80 | 44.8587 | 12.90 | 3.3791 | 95.00 | 114.2822 | 5.10 |
| 2.8840 | 102.70 | 45.2151 | 12.80 | 3.3868 | 94.90 | 116.5738 | 5.00 |
| 2.8893 | 102.60 | 45.5771 | 12.70 | 3.3946 | 94.80 | 118.9589 | 4.90 |
| 2.8946 | 102.50 | 45.9448 | 12.60 | 3.4025 | 94.70 | 121.4432 | 4.80 |
| 2.9000 | 102.40 | 46.3183 | 12.50 | 3.4103 | 94.60 | 124.0331 | 4.70 |
| 2.9054 | 102.30 | 46.6978 | 12.40 | 3.4183 | 94.50 | 126.7354 | 4.60 |
| 2.9108 | 102.20 | 47.0834 | 12.30 | 3.4262 | 94.40 | 129.5578 | 4.50 |
| 2.9162 | 102.10 | 47.4753 | 12.20 | 3.4342 | 94.30 | 132.5083 | 4.40 |
| 2.9217 | 102.00 | 47.8736 | 12.10 | 3.4422 | 94.20 | 135.5958 | 4.30 |
| 2.9272 | 101.90 | 48.2785 | 12.00 | 3.4503 | 94.10 | 138.8303 | 4.20 |
| 2.9327 | 101.80 | 48.6901 | 11.90 | 3.4584 | 94.00 | 142.2224 | 4.10 |
| 2.9382 | 101.70 | 49.1087 | 11.80 | 3.4666 | 93.90 | 145.7840 | 4.00 |
| 2.9438 | 101.60 | 49.5344 | 11.70 | 3.4748 | 93.80 | 149.5280 | 3.90 |
| 2.9494 | 101.50 | 49.9674 | 11.60 | 3.4830 | 93.70 | 153.4690 | 3.80 |
| 2.9550 | 101.40 | 50.4078 | 11.50 | 3.4913 | 93.60 | 157.6228 | 3.70 |
| 2.9607 | 101.30 | 50.8560 | 11.40 | 3.4996 | 93.50 | 162.0072 | 3.60 |
| 2.9663 | 101.20 | 51.3120 | 11.30 | 3.5080 | 93.40 | 166.6420 | 3.50 |
| 2.9720 | 101.10 | 51.7761 | 11.20 | 3.5164 | 93.30 | 171.5493 | 3.40 |
| 2.9778 | 101.00 | 52.2485 | 11.10 | 3.5249 | 93.20 | 176.7537 | 3.30 |
| 2.9835 | 100.90 | 52.7294 | 11.00 | 3.5334 | 93.10 | 182.2833 | 3.20 |
| 2.9893 | 100.80 | 53.2191 | 10.90 | 3.5419 | 93.00 | 188.1694 | 3.10 |
| 2.9952 | 100.70 | 53.7179 | 10.80 | 3.5505 | 92.90 | 194.4478 | 3.00 |
| 3.0010 | 100.60 | 54.2259 | 10.70 | 3.5591 | 92.80 | 201.1589 | 2.90 |
| 3.0069 | 100.50 | 54.7434 | 10.60 | 3.5678 | 92.70 | 208.3492 | 2.80 |
| 3.0128 | 100.40 | 55.2707 | 10.50 | 3.5765 | 92.60 | 216.0719 | 2.70 |
| 3.0187 | 100.30 | 55.8081 | 10.40 | 3.5853 | 92.50 | 224.3884 | 2.60 |
| 3.0247 | 100.20 | 56.3559 | 10.30 | 3.5941 | 92.40 | 233.3699 | 2.50 |
| 3.0307 | 100.10 | 56.9144 | 10.20 | 3.6029 | 92.30 | 243.0997 | 2.40 |
| 3.0367 | 100.00 | 57.4838 | 10.10 | 3.6118 | 92.20 | 253.6753 | 2.30 |
| 3.0427 | 99.90 | 58.0646 | 10.00 | 3.6208 | 92.10 | 265.2121 | 2.20 |
| 3.0488 | 99.80 | 58.6571 | 9.90 | 3.6298 | 92.00 | 277.8473 | 2.10 |
| 3.0549 | 99.70 | 59.2616 | 9.80 | 3.6388 | 91.90 | 291.7457 | 2.00 |

TABLE 1-continued

| w3/v (unitless) | Θ Lookup (deg) | d3/v (unitless) | Θ Lookup (deg) |
|---|---|---|---|
| 3.6479 | 91.80 | 307.1069 | 1.90 |
| 3.6570 | 91.70 | 324.1745 | 1.80 |
| 3.6662 | 91.60 | 343.2496 | 1.70 |
| 3.6754 | 91.50 | 364.7089 | 1.60 |
| 3.6847 | 91.40 | 389.0289 | 1.50 |
| 3.6940 | 91.30 | 416.8228 | 1.40 |
| 3.7034 | 91.20 | 448.8923 | 1.30 |
| 3.7128 | 91.10 | 486.3061 | 1.20 |
| 3.7223 | 91.00 | 530.5220 | 1.10 |
| 3.7318 | 90.90 | 583.5804 | 1.00 |
| 3.7414 | 90.80 | 648.4289 | 0.90 |
| 3.7510 | 90.70 | 729.4888 | 0.80 |
| 3.7606 | 90.60 | 833.7078 | 0.70 |
| 3.7704 | 90.50 | 972.6656 | 0.60 |
| 3.7801 | 90.40 | 1167.2053 | 0.50 |
| 3.7900 | 90.30 | 1459.0131 | 0.40 |
| 3.7998 | 90.20 | 1945.3586 | 0.30 |
| 3.8097 | 90.10 | 2918.0404 | 0.20 |
| 3.8197 | 90.00 | 5836.2355 | 0.10 |

In some embodiments, a software program or application may assess the contact angle. Software may assess if the measured diameter is greater than the 90°-diameter (d90) (Eq. [3]). If the measured diameter is greater than the 90°-diameter (d90) (Eq. [3]), then it is valid to use the Bikerman equation [1]. If the measured diameter is less than d90 a modified Bikerman equation [2] may be used, wherein the diameter of the widest portion of the drop is used instead of the base (or contact) diameter of the drop. In some embodiments a spreadsheet or dedicated software program may be employed to determine the contact angle using either equation [1] or equation [2] as determined to be valid via equation [3]. In some embodiments, a spreadsheet or software program may utilize a lookup-table (Tab. 1) of the Bikerman equation with 0.1° increments over the range of θ of 0.1° to 179.9° to return the contact angle value that matches the experimentally measured $d^3/v$ ratio.

Figure 2:
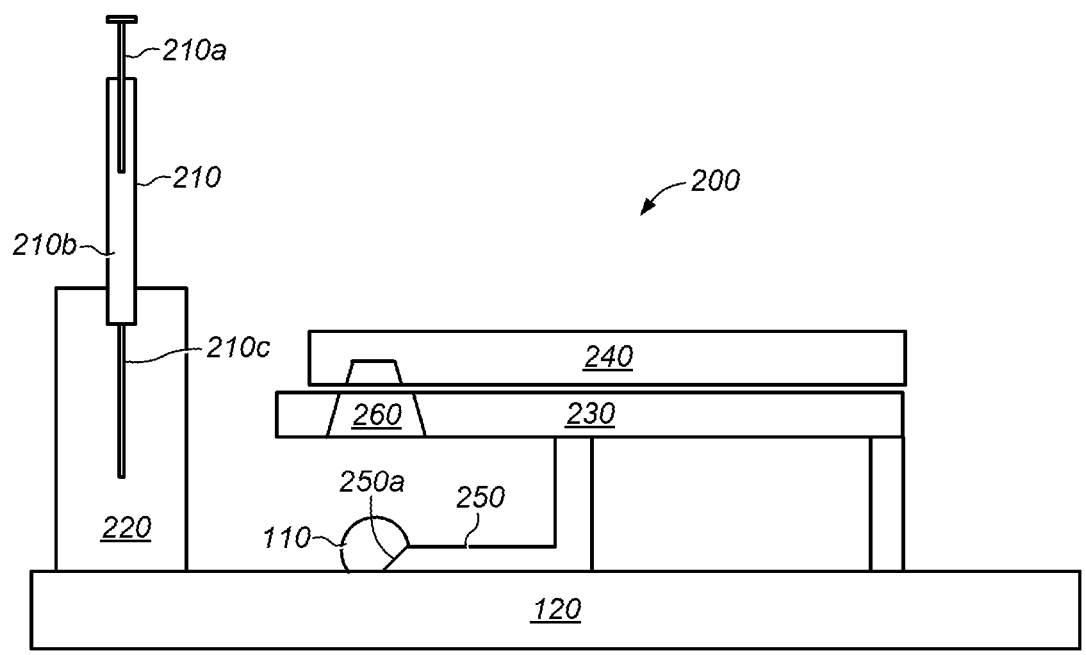
FIG. 2 depicts a side view of a representation of an embodiment of a portable system for assessing surface cleanliness including a dispensing device.

FIG. 2 depicts a side view of a representation of an embodiment of a portable system 200 for assessing surface cleanliness. In some embodiments, the system 200 may include a dispensing device 210. The dispensing device may dispense, during use, a measured amount of liquid on a surface forming a drop 110. In some embodiments, the dispensing device may include an accurate device. In some embodiments, the dispensing device may include a pump.

In some embodiments, the dispensing device 210 may include a syringe. A syringe may include a simple pump consisting of a plunger 210a that fits tightly in a tube 210b. The plunger may be pulled and pushed along an inside of a cylindrical tube, allowing the syringe to take in and expel fluids through an orifice at the open end of the tube. The open end of the syringe may be fitted with a hypodermic needle 210c, a nozzle, or tubing to help direct the flow into and out of the barrel.

In some embodiments, the dispensing device may include a stand 220. The stand may function to stabilize the dispensing device during use. The stand may allow a user to more accurately dispense a droplet onto a surface.

In some embodiments, the dispensing device may have a relative uncertainty of less than 5%. In some embodiments, the dispensing device may have a relative uncertainty of less than 2%. Relative uncertainty is calculated as the standard deviation divided by the mean value. This is also known as the relative standard deviation (RSD) in percent. Others call this the coefficient of variation (CV).

Figure 3:
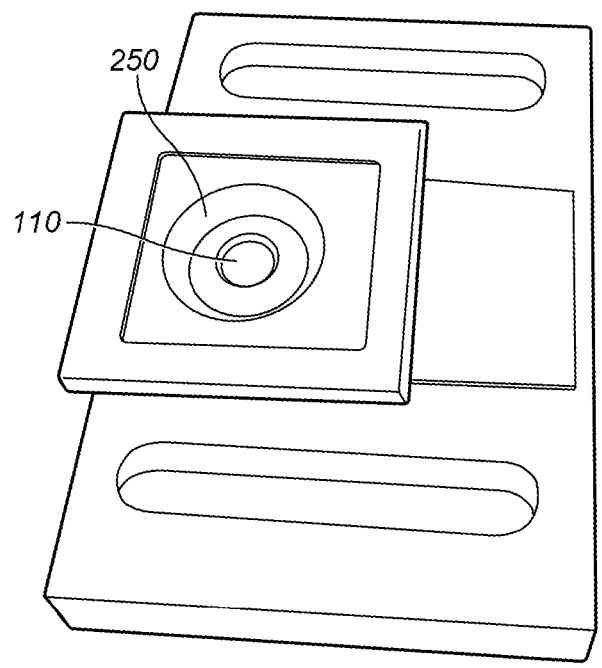
FIG. 3 depicts an upper perspective view of a representation of an embodiment of a calibration feature of known dimension.

In some embodiments, the system 200 may include a stage 230. The stage may support, during use, a digital imaging device 240. In some embodiments, the stage is coupled to the digital imaging device. In some embodiments, the system may include a calibration feature 250. The calibration feature may be of known dimension. The calibration feature may be coupled to the stage. The calibration feature may facilitate assessment, during use, of a dimension of the drop 110. The dimension may include a diameter of the drop. In some embodiments, the system is configured to assess a contact angle of the drop with the surface 120. FIG. 3 depicts an upper perspective view of a representation of an embodiment of a calibration feature 250 of known dimension in the form of a circular tapered opening surrounding the drop 110.

One or more dimensions of the calibration feature may be known. The known dimension may be used to assess one or more dimensions of the drop. The known dimension may be correlated to pixels from a digital image taken from the digital imaging device such that a dimension of the drop may be assessed by determining the number of pixels in the image associated with the dimension.

In some embodiments, the calibration feature may include a tapered edge 250a. A tapered edge may inhibit parallax. Parallax is a displacement or difference in the apparent position of an object viewed along two different lines of sight, and is measured by the angle or semi-angle of inclination between the two lines. Parallax affects optical instruments such as rifle scopes, binoculars, microscopes, and twin-lens reflex cameras that view objects from slightly different angles.

Figure 4:
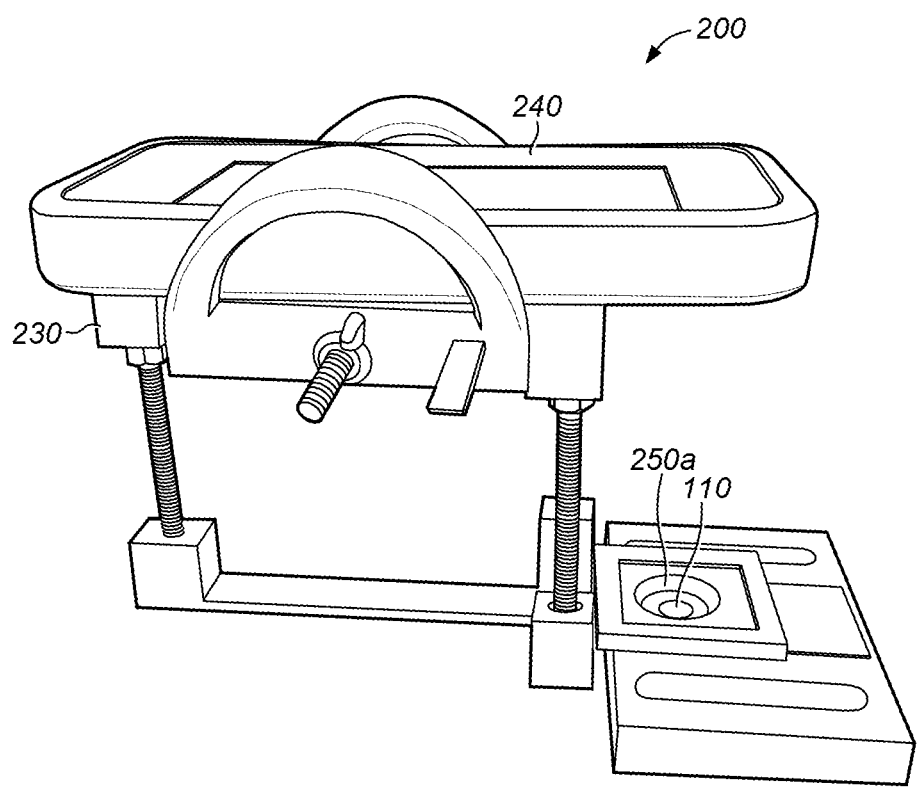
FIG. 4 depicts a perspective view of a representation of an embodiment of a portable system for assessing surface cleanliness.
Figure 5:
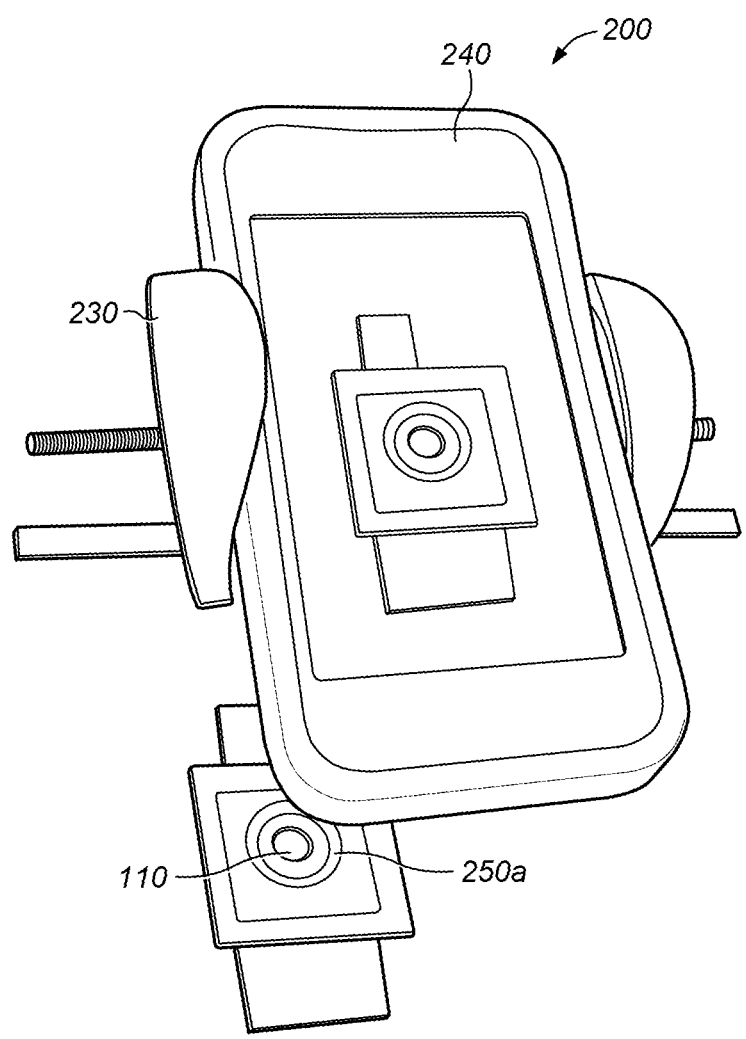
FIG. 5 depicts an upper perspective view of a representation of an embodiment of a portable system for assessing surface cleanliness.

FIGS. 4-5 depict perspective views of a representation of an embodiment of a portable system 200 for assessing surface cleanliness. In some embodiments, a distance between the stage and the calibration feature is determined by a focal length of the digital imaging device. This allows the drop and the calibration feature to be in focus. In some embodiments, a distance between the stage and the calibration feature is adjustable and determined by a focal length of the digital imaging device. A system for adjusting the distance may include systems which allow for incremental adjustment of the distance. In some embodiments, the system for distance adjustment may include threaded elongated members coupling the stage to the calibration feature. In some embodiments, the system for distance adjustment may include a ratcheting system coupling the stage to the calibration feature.

In some embodiments, the digital imaging device comprises a lens. The lens may include a macro or similar lens. A macro lens may allow the digital imaging device to focus on the drop and/or calibration feature.

In some embodiments, the stage includes a lens 260 (e.g., as depicted in FIG. 2) incorporated into the stage. The lens in the stage may function in combination with the digital imaging device. A distance between the stage and the calibration feature is determined by a focal length of the macro lens. In some embodiments, the stage includes the digital imaging device such that the stage and digital imaging device are one unit.

In some embodiments, the digital imaging device may include a digital camera. The digital image may include an electronic device which includes a digital camera (e.g., cellular phones, tablets, etc.).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A support for use during the measurement of physical properties of a drop of water on a surface, comprising:
    a stage which is capable of supporting, during measurement of the physical properties of the drop of water, a digital imaging device;
    a calibration feature of known dimension coupled to the stage, wherein the calibration feature is in the form of a circular opening; and wherein the calibration feature is positionable over the drop of liquid placed on the surface such that the calibration feature surrounds the drop of liquid;
    wherein, during use, a digital imaging device coupled to the stage is positioned by the stage such that the digital imaging device can, simultaneously, obtain an image of the drop of water and the calibration feature.

2. The support of claim 1, wherein a distance between the stage and the calibration feature is predetermined based on a focal length of the digital imaging device.

3. The support of claim 1, wherein a distance between the stage and the calibration feature is adjustable such that the distance can be set based on a focal length of the digital imaging device.

4. The support of claim 1, wherein the stage comprises a macro lens.

5. The support of claim 1, wherein the stage comprises a macro lens, and wherein a distance between the stage and the calibration feature is determined by a focal length of the macro lens.

6. The support of claim 1, wherein the digital imaging device comprises a multi-function device.

7. The support of claim 1, wherein the known dimension comprises a diameter of the circular opening.

8. The support of claim 1, wherein the circular opening of the calibration feature comprises a tapered edge.

9. A method of assessing surface cleanliness, comprising:
    dispensing a measured amount of liquid on a surface forming a drop using a dispensing device;
    placing a portable system for assessing surface cleanliness or surface energy over the drop, the portable system comprising:
        a stage which is capable of supporting a digital imaging device; and
        a calibration feature of known dimension coupled to the stage, wherein the calibration feature is in the form of a circular opening;
    positioning the portable system over the drop such that the calibration feature surrounds the drop; and
    capturing an image of the drop and the calibration feature.

10. The method of claim 9, further comprising determining a distance between the stage and the calibration feature using a focal length of the digital imaging device.

11. The method of claim 9, further comprising adjusting a distance between the stage and the calibration feature using a focal length of the digital imaging device.

12. The method of claim 9, further comprising assessing a contact angle of the drop with the surface using the captured image of the drop and the calibration feature.

13. The method of claim 12, further comprising assessing a cleanliness of the surface using the assessed contact angle.

14. The method of claim 9, wherein the stage comprises a macro lens.

15. The method of claim 9, wherein the known dimension comprises a diameter of the circular opening.

16. The method of claim 9, wherein the circular opening of the calibration feature comprises a tapered edge.

* * * * *